(12) United States Patent
Chattopadhyay et al.

(10) Patent No.: US 6,252,114 B1
(45) Date of Patent: Jun. 26, 2001

(54) PROCESS FOR PREPARING NOVEL BIOLOGICALLY ACTIVE SYNTHETIC MOLECULE 4-(P-METHOXYPHENYL)-2-AMINO-BUTANE

(75) Inventors: Sunil Kumar Chattopadhyay; Koneni Venkata Sashidhara; Vinayak Tripathi; Arun Kumar Tripathi; Veena Prajapati; Sushil Kumar, all of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/535,121

(22) Filed: Mar. 24, 2000

(51) Int. Cl.⁷ .................................................. C07C 207/00
(52) U.S. Cl. ........................................... 564/375; 564/387
(58) Field of Search ..................... 564/375, 387

(56) References Cited

U.S. PATENT DOCUMENTS

| | | | |
|---|---|---|---|
| 4,695,589 | * | 9/1987 | Philion . |
| 4,950,606 | * | 8/1990 | Stirling et al. . |
| 5,073,648 | * | 12/1991 | Hagishita . |
| 5,169,780 | * | 12/1992 | Stirling et al. . |
| 5,300,437 | * | 4/1994 | Stirling et al. . |

* cited by examiner

*Primary Examiner*—Samuel Barts
(74) *Attorney, Agent, or Firm*—Ratner & Prestia

(57) ABSTRACT

The invention provides a process for the preparation of 4-(p-methoxyphenyl)-2-aminobutane represented by structural formula (1) as shown herein below:

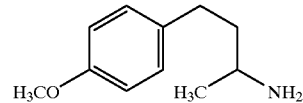

[$C_{11}H_{17}ON$=4-(p-methoxy phenyl)-2-amino butane]
said process comprising the steps of, (a) isolating a phenolic compound 4-hydroxyphenyl)-butan-2-ol from the leaves of *Taxus wallichiana* by known methods, (b) treating the phenolic compound in aqueous mineral acid to obtain a phenolic halide derivative, (c) converting the phenolic halide derivative into its methyl ether by treating it with a methating agent, (d) reacting the methyl ether halide with azide to obtain an azido derivative, and (e) hydrogenating the azido compound to obtain 4-(p-methoxyphenyl)-2-aminobutane.

6 Claims, No Drawings

PROCESS FOR PREPARING NOVEL BIOLOGICALLY ACTIVE SYNTHETIC MOLECULE 4-(P-METHOXYPHENYL)-2-AMINO-BUTANE

FIELD

The invention provides a process for preparing novel biologically active synthetic molecule 4-(p-methoxyphenyl)-2-amino-butane from a naturally occurring compound 4-(p-hydroxyphenyl)-butan-2-ol. The molecule of the invention is a colorless crystalline solid, having molecular formula, $C_{11}H_{17}ON$, and structural formula (1) as represented hereunder:

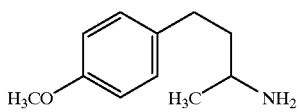

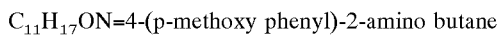

$C_{11}H_{17}ON$=4-(p-methoxy phenyl)-2-amino butane

The spectral characteristics of the molecule are as follows:

The EI mass spectrum of the compound showed its $M^r$ at M/Z 179, thus confirming its molecular formula as $C_{11}H17ON$, and other diagnostic fragment peaks at M/Z 162, 147, 121 and 91 IR$v_{max}$(KBr) 3360, 2940, 1610, 1515, 14501, 1030 and 850 cm$^{-1}$ The product is a new molecule which has been prepared from a readily available starting material 4-(p-hydroxyphenyl)-butan-2-ol having structural formula (2) isolated from the plant *Taxus wallichiana*.

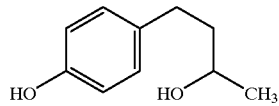

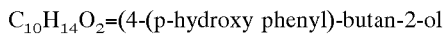

$C_{10}H_{14}O_2$=(4-(p-hydroxy phenyl)-butan-2-ol

BACKGROUND AND PRIOR ART

The plant *Taxus wallichiana* which also known as Himalayan yew is now considered to be one of the most needed plants for commercial exploitation as it contains the anticancer drug Taxol. Taxol, a highly oxygenated diterpenoid molecule and potent anticancer drug was first isolated from the stem bark of *Taxus brevifolia*. Thereafter, it has also been isolated from other Taxus plants including the Himalayan yew *Taxus wallichiana*.

The applicants have been working on different parts of *Taxus wallichiana* collected from different pairs of India for the isolation of taxol, its important analogues and precursor 10-deacetyl baccatin III (DAB); During the course of investigation, the applicants have isolated a major compound from the leaves of *Taxus wallichiana*. The major compound was identified as 4-(p-hydroxyphenyl)-butan-2-ol having structural formula (2). This compound can be obtained with a yield of 0.2% from the leaves of *Taxus wallichiana*. Accordingly, the applicants have developed a simple and cost effective process for isolation of this compound from the leaves of *T. wallichiana*. The process of isolation of the compound comprises the steps of defatting air dried pulverised Taxus leaves with aliphatic hydrocarbon solvents, extracting the defatted leaves with chlorinated solvents and polar solvents successively, concentrating the chlorinated solvent soluble fraction to a residue and treating the residue with aqueous solution of alkali and isolating the compound from the alkali soluble fraction by acidifying it and extracting it with ethyl acetate, to obtain 4-(p-hydroxy phenyl)-butan-2-ol.having structural formula (2).

The compound (2) was not found to be active in bioassay studies for evaluation of growth inhibition and antifeedant activity. The compound of formula (2) was obtained with high yield (0.2%), converted into other structural analogues through a series of chemical reactions. In the course of this investigation, the applicants were able to prepare a new molecule represented by formula (1) from 4-(p-hydroxy phenyl)-butan-2-ol, represented by formula (2). The compound having structural formula (1) shows significant activity as a growth inhibitor and antifeedant.

The compound having formula (1) was evaluated as feeding deterrant and growth inhibitor against $4^{th}$ in star larvae of Spilarctia Obliqua. This insect attacks more than twenty cash crops including urd, mong, arhar, mint and coleus etc.

Compound having formula (1) is non hazardous in nature and thus is ecologically safe and environmentally sound for its use as an agrochemical.

OBJECTS

The main object of this invention is to provide a new molecule, 4-(p-methoxyphenyl)-2-amino butane represented by formula (1) and represented by the molecular formula $C_{11}H_{17}ON$.

Another object of the present invention is to provide a process for the preparation of this biologically active compound represented by structural formula (1) with higher yields, from a readily available starting material isolated from the plant *Taxus wallichiana*.

Yet, another object of the present invention is to obtain this important molecule through a process which avoids the use of chromatographic separation and makes the process cost effective.

DETAILED DESCRIPTION

Accordingly, the present invention provides a process for the preparation of a novel molecule 4-(p-methoxyphenyl)-2-amino butane, represented by formula (1) and having growth inhibitory and antifeedant activity. The process for the isolation of 4-(p-methoxyphenyl)-2-amino butane comprises the steps of:

a) isolating the phenolic compound represented by structural formula (2) from the leaves of *Taxus wallichiana* by known methods, b) treating the compound having formula (2) in aqueous mineral acid at 25–100° C. for 2–10 hours to obtain a phenolic halide derivative represented by structural formula (3), c) converting the phenolic halide derivative into its methyl ether by treating it with a methylating agent to obtain a methyl ether halide represented by structural formula (4), d) reacting the methyl ether formed with azide into an azido derivative having structural formula (5), and e) hydrogenating the azido compound of step (d) by catalytic hydrogenation in the presence of a catalyst in lower aliphatic alcohol to obtain 4-(p-methoxyphenyl)-2-amino butane represented by structural formula (1).

The aqueous mineral acid used in step (b) is selected from the group consisting of hydrochloric acid, hydrobromic acid and hydroiodic acid. The methylating agent used in step (c) is selected from methyl iodide or dimethyl sulphate.

The azide, used in step (d) is sodium azide or trimethyl silyl azide.

The catalyst used in the hydrogenation process is selected from palladium charcoal and platinum oxide. The lower aliphatic alcohol used as medium to dissolve the azide derivative in the hydrogenation process may be methyl alcohol, ethyl alcohol.

As mentioned earlier, the compound 4-(p-methoxy phenyl)-2-amino butane exhibits antifeedant and growth inhibiting activity against certain insects, especially the larvae of Spilarctia Obliqua.

Hence, the compound has potential use as an insecticide, and would have wide spread applications in insecticidal compositions. Without wishing to be bound by any theory, the Applicants state that an insecticidal composition comprising an effective amount of the compound 4-(p-methoxyphenyl)-2-amino butane and an adjuvant in an amount sufficient to enhance the activity of the composition may be prepared. In practice, it is found that the novel compound 4-(p-methoxyphenyl)-2-amino butane per se may also be used to control insects in fields, though it is recommended that the compound be mixed with augmenting adjuvants such as distilled water, acetone or such other solvents before use. The insecticidal compositions may be sprayed or applied in the soil for control of pests. Further, the said insecticidal composition may be effectively used for the control of insects/their larvae such as Spilarctia Obliqua. In practice, the compound is found to be very useful in controlling phytopathogenic insects and mites.

The invention is described in detail in the examples given below which are provided to illustrate the invention and therefore should not be construed to limit the scope of this invention.

The products of the reactions as described in the steps hereinbelow is represented hereunder:

Step 1

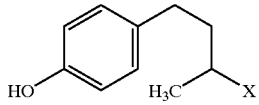

(X = Br or Cl or I)

$C_{10}H_{13}OX$(4-(p-hydroxyphenyl)-2-halobutane(3)

Step 2

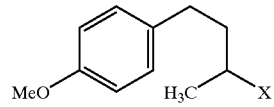

(X = Br or Cl or I)

$C_{11}H_{15}OX$(4-(p-methoxyphenyl)-2-halo-butane) (4)

Step 3

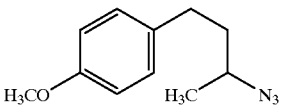

$C_{11}H_{15}ON_3$=(4-(p-methoxyphenyl)-2-azido butane). (5)

Step 4

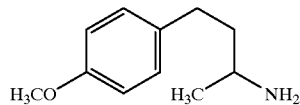

$C_{11}H_{17}ON$=(4-(p-methoxyphenyl)-2-amino butane (1)

EXAMPLE 1

Step 1

Preparation of (4-p-hydroxyphenyl)-2 bromobutane (represented by structural formula (3) ($C_{10}H_{13}O$ Br)

In a 50 ml conical flask was charged with compound of formula (2) (1 gm) and to it was added HBr (44%) (5 ml) dropwise and the reaction mixture was refluxed for 6 hours at 80° C. with constant stirring. The reaction mixture was diluted with excess water and extracted with ethyl acetate (25 ml×3); The ethyl acetate was dried over anhydrous sodium sulphate and concentrated. The oily residue thus obtained above was subjected to column chromatography over silica gel to get pure compound having formula (3) (1 gm).

Step 2

Preparation of (4-(p-methoxyphenyl)-2-bromobutane(4).

The compound having formula (3) (1 g) was dissolved in acetone (10 ml) and to it were added anhydrous potassium carbonate (10 g) and dimethyl sulphate (3 ml) and refluxed with stirring for 4 hours. Water was added to the reaction flask and stirred for 3 hours. It was then extracted with $CHCl_3$ (25 ml×3) and washed with water (25 ml×2). The organic layer was dried over anhydrous sodium sulphate and concentrated in vaccuo to get oily material viz compound having structural formula (4) (1.0 g).

Step 3

Preparation of 4-(p-methoxyphenyl)-2-azido-butane ($C_{11}H_{15}ON_3$)

Compound having formula (4) (1.0 g) was dissolved in DMF (10 ml) and treated with sodium azide (2 g) and stirred at 20–80° for 6 hours. The reaction mixture was poured in water and extracted with benzene (50 ml×3); the organic layer was washed with water (25 ml×2, dried over sodium sulphate and concentrated to obtain 800 gm of the compound having structural formula (5).

Step 4

Preparation of 4-(p-methoxyphenyl)-2-amino-butane ($CH_{11}H_{17}ON$)

The azide compound having structural formula (5) (300 mg) was dissolved in methanol (20 ml) and to it was added palladium charcoal (30 mg) and stirred under hydrogen for 6 hrs at 55 Psi; catalyst was then filtered off, the filtrate was concentrated to give a residue which crystallized from acetone-hexane mixture as needles to give compound having structural formula (1) (208 mg).

EXAMPLE 2

Step 1

Preparation of (4-(p-hydroxyphenyl)-2-chlorobutane ($C_{10}H_{13}OCl$) having structural formula (3).

In a 50 ml conical flask was charged with compound having formula 2 (1 g) and to it added HCl 37% 5 ml dropwise and the reaction mixture was refluxed for 6 hours at 80° C. with constant stirring. The reaction mixture was diluted with excess water and extracted with ethyl acetate (25 ml×3). The ethyl acetate extract was dried over anhydrous sodium sulphate and concentrated. The oily residue thus obtained was subjected to flash chromatography over fluorosil to give pure compound having formula (3) (1 g).
Step 2

Preparation of (4-(p-methoxyphenyl)-2-chlorobutane ($C_{11}H_{15}OCl$) represented by formula (4).

The compound (3) (1 g) was dissolved in acetone (10 ml) was dissolved in acetone (10 ml) and to it were added anhydrous potassium carbonate (10 g) and methyl iodide (3 ml) and refluxed with stirring for 4 hours, water was added to the reaction flask and was stirred for 3 hours. It was then extracted with water $CHCl_3$ (25 ml×3) and washed with water (25 ml×2). The organic layer was dried over anhydrous sodium sulphate and concentrated in vaccuo to get oily material, the compound having formula (4) (1 g).
Step 3

Preparation of 4-(p-methoxy phenyl)-2-azido-butane ($CH_{11}H_{15}ON_3$) represented by the formula (5).

Compound (4) (1.0 g) was dissolved in DMF (10 ml) and treated with trimethyl silyl azide (2 g) and stirred at 20–80° C. for 6 hours. The reaction mixture was poured in water and extracted with benzene (50 ml×3); The organic layer was washed with water (25 ml×2); dried over anhydrous sodium sulphate and concentrated to give azide compound having structural formula (5) (800 mg).
Step 4

Preparation of 4-(p-methoxy phenyl)-2-amino butane ($C_{11}H_{17}ON$) having formula (1).

The azide compound of formula (5) (300 mg) was dissolved in ethanol (20 ml) and to it was added $PtO_2$ (10 mg) and stirred under hydrogen for 6 hours at 55 Psi; catalyst was then filtered off, filtrate was concentrated to give a residue which crystallized from acetone hexane mixture as needless to give 208 mg of compound having formula (1).

The spectral characteristics of the molecule are as follows:

The EI mass spectrum of the compound showed its $M^+$ at M/Z 179, thus confirming its molecular formula as $C_{11}H_{17}ON$, and other diagnostic fragment peaks at M/Z 162, 147, 121, and 91 $IRv_{max}$(KBr) 3360, 2940, 1610, 1515, 14501, 1030 and 850 $Cm^{-1}$.

The molecule has been prepared from readily available starting material 4-(p-hydroxyphenyl)-butan-2-ol having formula (2) isolated from the plant *Taxus wallichiana*.

Evaluation of the Novel Molecule for Antifeedant Activity

The compound having formula (1) was evaluated as feeding deterrent and growth inhibitor against $4^{th}$ instar larvae of spilarctia obliqua (Bihar hairy caterpillar). This insect attacks more than twenty cash crops like urd, moong, arhar, mint and coleus etc. Several synthetic insecticides like quinalphos, Phosphamidon and synthetic pyrethroids are commercially used to manage this insect pest. But, the insect is developing resistance towards some of these insecticides. Therefore, it has now become imperative to search for new ecologically safe, environmentally sound and non-toxic chemicals to manage this pest.

With compound having formula (1) insect feeding deterrency and growth inhibition was tested by diet-mix method.

In this method, 4-methoxy-aryl-2-amino-butane the compound having formula (1) was dissolved in acetone to make various concentrations ranging from 1000 to 5000 ppm. Test solution was mixed in the artificial diet of the insect so that each gram of diet contained 60–300 µg of the compound (1). $4^{th}$ instar larva (newly moulted) starved four hours, was weighed and released on treated artificial diet in thirty replications. In control, only solvent acetone was mixed and azadirachtin at 1000 ppm concentration was taken as standard for feeding bioassay. After 24 hours, number of faecal pellets produced were counted, and the data were analyzed for % feeding deterrency. Some experiments were continued for next 24 hours and weights of the larva were taken daily. After 3 days, experiment was discontinued and weight gain or loss was analyzed for % growth inhibition.

Diflubenzuron at 5 ppm was taken as a standard in case of growth inhibitory assay. The test result of compound having formula (1) in terms of its feeding deterrency and growth inhibition as compared to standards azadirachtin and diflubenzuron are given in table 1.

TABLE 1

| Compound | Concentration (ppm) | % feeding deterrency | % growth inhibition |
| --- | --- | --- | --- |
| Compound 1 | 1000 | 32.0 | 48.0 |
|  | 2000 | 40.0 | 59.0 |
|  | 3000 | 64.0 | 72.0 |
|  | 4000 | 82.0 | 100.0 |
|  | 5000 | 100.0 | 128.0 |
| Azadirachtin | 1000 | 100.0 | — |
| Diflubenzuron | 5 | — | 100.0 |

As it appears from the table 1, compound having formula (1) is less active as a feeding deterrent agent as compared to azadirachtin. However, the new molecule (1) has several other advantages over azadirachtin which include:

(a) Compound having formula (1) is a very small molecule (molecular weight 179), structurally as compared to azadirachtin which is a large molecule with many chiral centres, molecular weight 720; therefore, the molecule (1) can be synthesized easily as compared to azadirachtin, the synthesis of which would never be commercially viable.

(b) Unlike azadirachtin which is photosensitive i.e., it decomposes on exposure to sun light, compound having formula (1) is not sensitive to light (both UV and sunlight). Therefore, compound (1) can be used under field condition in contrast to azadirachtin which can not be used under field condition till to date.

In terms of growth inhibitory properties, compound having formula (1) is less active than the standard compound diflubenzuron. However, many insects are developing resistance to this particular compound and therefore higher doses are required to kill the insects as compared to 5 ppm as mentioned in table 1. Ultimately its effectiveness will be stopped.

Therefore, compound having formula (1) which is structurally different from diflubenzuron will be useful against diflubenzuron resistant insects.

Also, diflubenzuron contains fluorine atoms in its molecule and therefore it is prone to be carcinogenic and environmentally hardazous on microbial activation. Due to its different structure as compared to diflubenzuron, compound having formula (1) will be ecologically non hazardous and environmentally sound.

From the foregoing, it will be clear that the compounds of the invention have extremely high controlling effects against various types of phytopathogenes insects, mites etc and thus are useful as active ingredients of agricultural and horticultural insecticides, miticides etc.

Advantages

1. The chemicals and reagents that are used to prepare the active compound are not expensive and thus the process is cost effective and viable for commercial production.
2. All the steps in the process are straight forward; No extreme reaction conditions are necessary to be maintained for preparation of the active compound and thus the process will be commercially viable.

What is claimed is:

1. A process for preparation of 4-(p-methoxyphenyl)-2-aminobutane represented by the structural formula as shown herein below:

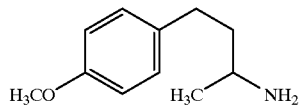

having the formula $C_{11}H_{17}ON$, said process comprising the steps of:
  (a) isolating a phenolic compound (4-p-hydroxyphenyl)-butan-2-ol having the formula $C_{10}H_{14}O_2$
from the leaves of *Taxus wallichiana* by known methods,
  (b) treating the compound in aqueous mineral acid at 25–100° C. for 2–10 hours to obtain a phenolic halide derivative having the formula $C_{10}H_{13}OX$,
  (c) converting the phenolic halide derivative into its methyl ether by treating it with a methating agent to obtain a methyl ether halide having the formula $C_{11}H_{15}OX$,
  (d) reacting the methyl ether halide thus obtained with azide to obtain an azido derivative having the formula $C_{11}H_{15}ON_3$, and
  (e) hydrogenating the azido compound thus formed by catalytic hydrogenation in presence of a catalyst in lower aliphatic alcohol to obtain a compound having the formula $C_{11}H_{17}ON$, wherein X is selected from the group consisting of bromine, chlorine and iodine.

2. A process as claimed in claim 1 wherein the aqueous mineral acid in step (b) is selected from hydrochloric acid, hydrobromic acid and hydroiodic acid.

3. A process as claimed is claim 1 wherein the methylating agent in step (c) is selected from methyl iodide and dimethyl sulfate.

4. A process as claimed in claim 1 wherein the azide in step (d) is selected from sodium azide and trimethyl silyl azide.

5. A process as claimed in claim 1 wherein the catalyst in step (e) is selected from palladium charcoal and platinum oxide.

6. A process as claimed in claim 1 wherein the lower aliphatic alcohol is selected from methyl alcohol or ethyl alcohol.

* * * * *